(12) United States Patent
Chernoguz et al.

(10) Patent No.: US 7,133,711 B2
(45) Date of Patent: Nov. 7, 2006

(54) METHOD AND SYSTEM FOR DECOMPOSITION OF MULTIPLE CHANNEL SIGNALS

(75) Inventors: Naum Chernoguz, Nahariya (IL); Yevgeni Seider, Rehovot (IL)

(73) Assignee: Orsense, Ltd., Rehovot (IL)

( * ) Notice: Subject to any disclaimer, the term of this patent is extended or adjusted under 35 U.S.C. 154(b) by 515 days.

(21) Appl. No.: 10/635,922

(22) Filed: Aug. 7, 2003

(65) Prior Publication Data

US 2004/0116788 A1    Jun. 17, 2004

Related U.S. Application Data

(60) Provisional application No. 60/401,349, filed on Aug. 7, 2002.

(51) Int. Cl.
*A61B 5/00*    (2006.01)

(52) U.S. Cl. ............ 600/322; 600/310; 600/323; 600/330

(58) Field of Classification Search .......... 600/316, 600/322, 323, 324
See application file for complete search history.

(56) References Cited

U.S. PATENT DOCUMENTS

| | | | | |
|---|---|---|---|---|
| 5,193,543 A | * | 3/1993 | Yelderman | ............ 600/310 |
| 6,151,516 A | * | 11/2000 | Kiani-Azarbayjany et al. | ............ 600/322 |
| 6,400,972 B1 | | 6/2002 | Fine | |
| 6,587,704 B1 | | 7/2003 | Fine et al. | |

OTHER PUBLICATIONS

Chernoguz, Naum, *Tracking and Recovering Multiple Sinusoids by an Adaptive Resonator Bank*, Proc. of the Fourth IASTED International Conference, Signal and Image Processing, (Aug. 12-14, 2002, Kaua'i, Hawaii, USA), p. 49-54.

Goodwin, Graham, et al., *Sinusoidal Disturbance Rejection with Application to Helicopter Flight Data Estimation*, IEEE Trans. Acoustics, Speech, and Signal Processing, Jun. 1986, vol. 34(3), p. 479-484.

* cited by examiner

*Primary Examiner*—Eric Winakur
*Assistant Examiner*—Etsub D. Berhanu
(74) *Attorney, Agent, or Firm*—Browdy and Neimark, PLLC

(57) ABSTRACT

A method and a system for decomposition of a multiple channel signal reflecting characteristics of a blood perfused fleshy medium is provided. This technique can be utilized for determination of at least one desired blood parameter. According to the method a portion of the medium is illuminated by amplitude-modulated light of more than two different optic channels having wavelength in a range where the scattering properties of blood are sensitive to light radiation. Further, a light response of the medium sensed, and the multiple channel signal is generated. Thereafter, the multiple channel signal is analyzed that includes: filtering the multiple channel signal and separating at least a part of multiple channels from each other, and providing time evolutions of the light responses of the medium for the part of said multiple channels. According to the invention, the amplitude-modulated light is activated in a composite mode regime employing a combination of parallel and serial modes. The filtering of said multiple channel signal and the separating of said multiple channels from each other both includes applying an adaptive resonator bank to the multiple channel signal.

25 Claims, 8 Drawing Sheets

METHOD AND SYSTEM FOR DECOMPOSITION OF MULTIPLE CHANNEL SIGNALS

FIELD OF THE INVENTION

This invention relates to instrumentation and related methodology for measurements of an optic composite noisy signal, and in particular, for tracking and recovering multiple sinusoids from a multiple-wavelength signal generated by a photodetector.

BACKGROUND OF THE INVENTION

The problem of tracking and recovering multiple sinusoids from an optic multiple-wavelength signal is of high practical importance. For example, this problem arises in the non-invasive measurements of various blood parameters, e.g., blood oxygenation, that employ the detection of light transmitted or reflected from the location on the patient's body under measurement, and indication of the presence of various blood constituents based on known spectral behaviors of these constituents. Most of these techniques utilize a measurement optical device or probe attached to the patient's finger, which includes an optical assembly including a block of light emitting devices (e.g., LED) for irradiating the finger with light, and a photodetector (PD) for detecting the finger's light response. One of the conventional devices of the kind specified, such as a pulse oximeter, which is the generally accepted standard of everyday clinical practice, provides for measuring enhanced optical pulsatile signals caused by the changes in the volume of a blood flowing through a fleshy medium (e.g., finger). In conventional pulse oximeters as well as in other plethysmographic devices, an optical, amplitude-modulated light passes through the investigated sample (e.g., finger) at several (usually 2–3) different carrier wavelength (channels). Thereafter, a relationship between the intensities of the corresponding light responses is measured for determining the corresponding blood parameters. This technique utilizes the fact that different wavelength optic signals (channels) are transmitted differently, when passing through the sample, in accordance with the scattering and/or absorbing properties of the blood. In such techniques, the intensity of the signal obtained from the blood measurements (e.g., the intensity of photo-plethysmographic signal (PPS)) for the particular optical wavelength is obtained by means of a modulation-demodulation (M-D) procedure. For this purpose, the light emitting devices are switched on and off at a presumed rate (e.g., about 3–10 kHz), providing thereby a sequence (train) of light pulses for modulation of the corresponding carrier waves. The total pulsatile optical signal is detected by the photodetector and demodulated. The wavelength-related intensities are then derived from the demodulated optical signals.

In such conventional techniques, LEDs usually operate in one of two regimes, serial or parallel. In the serial mode regime, the operation of LEDs is separated in time. On the other hand, in the parallel mode regime, the LEDs are activated concurrently, but with the diverse modulation rates, or, in other words, the LED signals are separated in the frequency domain. The demodulation procedure used for separating different optic channels from each other is usually based on employing a bank of frequency-selective filters arranged either in cascade or parallel configurations.

More specifically, in the serial operation mode regime, each LED oscillates over a certain, relatively long period (including about 10–30 on-off LED ignition cycles), while the other LEDs are kept inactive over this period. An output signal, sensed by the photodetector, is then demodulated and associated with the corresponding wavelengths. Such a procedure is repeated for the next LED, et cetera.

In fact, the complexity of the modulation-demodulation technique rapidly increases with the number of the desired optical channels. Because of this, a majority of the commercial oximeters utilize few, e.g., 2–3 wavelengths. When such a relatively small number of optical channels is used, one can conduct PPS measurements for different optic channels in series, one by one. In such a case, as described above, each LED is activated serially over a certain period, used for demodulation, thus outputting a modulated signal related to the particular wavelength.

However, there are several critical points behind the serial mode regime. As the number of channels increases (e.g., close to ten), then the serial order comes into conflict with the required access rate. In other words, the physical and chemical processes, e.g., aggregation of red blood cells, occurring in the measured sample can be different for the time periods corresponding to the activation of different LEDs.

One of the shortcomings associated with the serial operation mode regime is the phase shift between the optical channels. Thus, the train of pulses (provided by a generator for LEDs' activation) switches between different LEDs by means of a multiplexer (MUX) such that only a single LED operates at a time. To this end, the longer LED operation period the higher delay between the different channels.

On the other hand, decreasing periods of LED activity restricts the demodulator selectivity and accuracy. So, in the serial mode, the demodulator selectivity and accuracy are in contradiction with the measuring process simultaneity.

Moreover, the serial mode regime yields various problems in signal processing. In this connection, it should be noted that the signal obtained from the blood measurements is usually affected by the electrical 50 Hz interference, lamp-induced 100 Hz optical noise, RF, and other disturbances. Hence, in the serial operation mode, the continuous interference and trends, that affect the output of the photodetector, cannot be rejected properly, because each channel, containing a part of the interference, is processed periodically and independently. A conventional prefiltering of the photodetector's output (in order to enhance the integral signal before the channel separation) breaks the independence between the consequent signal frames.

Replacing the serial order in optic by a parallel order in the conventional techniques leads to classical frequency-separation methods. In the parallel operation mode regime, all LEDs are activated concurrently, however with different switching rates. The further recovering of different optic channels from the composite signal (when the number of channels is small) is usually performed by means of a frequency-selective filter-bank.

It should be noted that in parallel mode regime, prefiltering as well as other conventional signal enhancing methods may generally become feasible. Nevertheless, in spite of the flexibility and universality, this regime becomes impractical when the number of wavelengths increases significantly, e.g. more than three.

For example, in the parallel operation mode regime the frequency spectrum lines (optic channels) should preferably be placed as far as possible from each other. This requirement can be hardly satisfied in practice for the case of a large number of LEDs. More specifically, a modulation-demodulation concept should meet the given technical restrictions.

In practice, the modulation process is formed by triggering the LEDs at a certain rate. Thus, on the one hand, the LED triggering rate is restricted, for example, by the transient of the photodetector circuitry. On the other hand, it should be taken into account that the resulting signal may be of a rather complex form and a care should be taken that the spectra do not intersect. In particular, since the output LED signals are non-sinusoidal (i.e., nearly square waves), some harmonies of the low-rate LEDs may interfere with the fundamentals belonging to high-rate LEDs. In other words, the first and second harmonics of the slowest LED determine the interval of possible modulation rates. Hence, all the other triggering rates should be distributed properly within his restricted interval. For instance, if the lowest modulation rate is defined at 2000 Hz, then (for example for the case of ten optic channels) the remaining nine on-off LEDs' rates should be placed in the interval between 2000 Hz and its second harmonic 4000 Hz. Thus, for the nine channels the frequencies can be placed over equally spaced 200 Hz increments at points such as: 2200, 2400, . . . , 3800 Hz. It should therefore be appreciated that as a number of the optic channels increases, the frequency distance between the modulated signals decreases, thereby causing the interference problem. Thus, in the case of multiple optic channels, the parallel operation mode may result in a "crowd" signal with closely spaced and strongly coupled components.

Moreover, due to the deviations from linearity in the signal acquisition and transformation tract all harmonics may interfere in the multi-channel system, thus producing the difference and sum of the frequencies. In practice, the signal spectrum comprises not only the first and higher harmonics, but their combinations as well, i.e., multiple sub-harmonics. The latter may fall close to the fundamental frequency, thus increasing the complexity of the signal decomposition in the parallel mode.

Next, the parallel mode regime may yield a corresponding extra complexity of the circuitry of the multi-channel system, because the number of the wires coupled to the probe grows in direct proportion with the number of the optic channels.

Moreover, the concurrent run of several LEDs can cause the overloading (saturation) of the photodetector, thus restricting the signal-to-noise ratio for each particular wavelength.

Another difficulty associated with utilization of the conventional parallel mode regime in signal decomposition techniques is in the fact that the sensed optical intensity may crucially differ for different channels. Thus, the channel separation problem can be compounded by the interference between the closely spaced strong and weak signals.

Due to the aforementioned disadvantages and also other known in the art reasons, a utilization of the pure parallel mode regime in multi-channel optical systems is impractical.

Concluding the above consideration, neither pure serial operation mode regime nor parallel mode regime alone is a reasonable and practical candidate for the system that intend to use a large number of wavelengths. Hence, when a multi-channel signal acquisition is of interest, a more sophisticated technique should be advantageous.

SUMMARY OF THE INVENTION

Thus, there is still a need in the art for, and it would be useful to have a novel method and a system for tracking and recovering multiple sinusoids from a multi-channel signal reflecting characteristics of a blood perfused fleshy medium.

It would be advantageous that such a technique could decompose the signal having a high level of optical disturbances and trends. Moreover, the technique should, inter alia, take into account the fact that the output waveforms of the light sources (e.g., LEDs) are not ideally square and may vary in shape from LED to LED. Since these shapes are not fixed and may vary due to the light intensity, temperature, etc., the technique should take into account that the signal sensed by a photodetector can be rich in harmonics that cannot be ignored.

It would also be desirable that the system for the measurements of blood parameters be properly adjusted, in order to combine several requirements, such as, high modulation rate, continuity of measurements for each wavelength, simultaneity, selectivity, etc.

The present invention satisfies the aforementioned need by providing a novel measuring system for determining blood parameters of a blood perfused fleshy medium. The system includes a generator, a multiplexer (MUX) coupled to the generator, a measuring probe coupled to the MUX and an analyzer coupled to the probe and, preferably, to the MUX. The generator is for providing a train of activating pulses. The MUX is configured for switching said activating pulses between different optic channels. The MUX is adapted for providing a composite mode regime for the activating pulses. The composite mode regime represents a combination of parallel and short serial modes of the activating pulses. The probe includes an illumination assembly having a plurality of light sources coupled to the MUX and activated by the activating pulses that provide ignition of the light sources. The light sources are configured for generating amplitude-modulated light of more than two different optic channels having wavelength in a range where the scattering properties of blood are sensitive to light radiation. The probe also includes a photodetector adapted for sensing a light response of the medium and generating a multiple channel signal reflecting blood characteristics.

The analyzer is configured for analyzing the multiple channel signal generated by the photodetector. The analyzer includes an analog-to-digital converter, a first decimator, a digital signal processor having an adaptive resonator bank unit, an output filtering unit, and a second decimator unit. The adaptive resonator bank unit is configured for (i) filtering the multiple channel signal out of trend signals, optical and electrical disturbances along with noise and (ii) separating the multiple channels from each other. The adaptive resonator bank unit is a closed-loop resonator bank, based on the spectral observer scheme, and coupled to the frequency adaptation loop. The output filtering unit is configured for obtaining synchronous in time evolutions of the light responses of the medium for the multiple channels. The second decimator is designed for outputting the time evolutions of the light responses at a lower sampling rate (e.g., 25–30 sample/sec), which may be required for certain applications.

The present invention also satisfies the aforementioned need by providing a method for decomposition of a multiple channel signal reflecting characteristics of a blood perfused fleshy medium. The method can, inter alia, be used for determination of desired blood parameters.

The method includes the step of illuminating a portion of the medium by amplitude-modulated light of more than two different optic channels. The light has wavelengths in a range where the scattering properties of blood are sensitive to light radiation. The amplitude-modulated light is activated in a composite mode regime representing a combination of parallel and serial modes of ignition of the light sources.

According to one example, the composite mode regime is a short serial mode regime, where each light source is modulated over a short interval, e.g., 1–5 on-off light ignition cycles.

According to another example, the composite mode regime is a short serial-parallel mode regime. In this regime, the light sources can be divided into two or more groups, where each group is operated in the short serial mode, however, with a different rate.

According to yet another example, the composite mode regime is a mixed-rate short serial mode regime. In this regime, at least two pulse trains having different rates are initially mixed, thereby resulting in a single complex-frame signal, and then applied to all the light sources at a certain time moment in the short serial mode regime.

The method also includes the step of sensing a light response of the medium and generating the multiple channel signal reflecting blood characteristics. Further, the method includes the step of analyzing the multiple channel signal. In turn, the analyzing of the multi-channel signal includes analog-to-digital conversion and decimating the signal. Moreover the analyzing of the multiple channel signal includes filtering the multiple channel signal and separating the multiple channels from each other. Both the filtering and separating are carried out by applying the adaptive resonator bank to the multiple channel signal. The analyzing also includes providing time evolutions of the light responses of the medium for the multiple channels.

Finally, the method comprises the step of deriving at least one blood characteristic parameter as a relation between the different time evolutions of the light responses (light intensity signals) of the medium obtained by filtering sinusoid signals corresponding to the optic channels.

There has thus been outlined, rather broadly, the more important features of the invention in order that the detailed description thereof that follows hereinafter may be better understood. Additional details and advantages of the invention will be set forth in the detailed description, and in part will be appreciated from the description, or may be learned by practice of the invention.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF THE INVENTION

Figure 1:
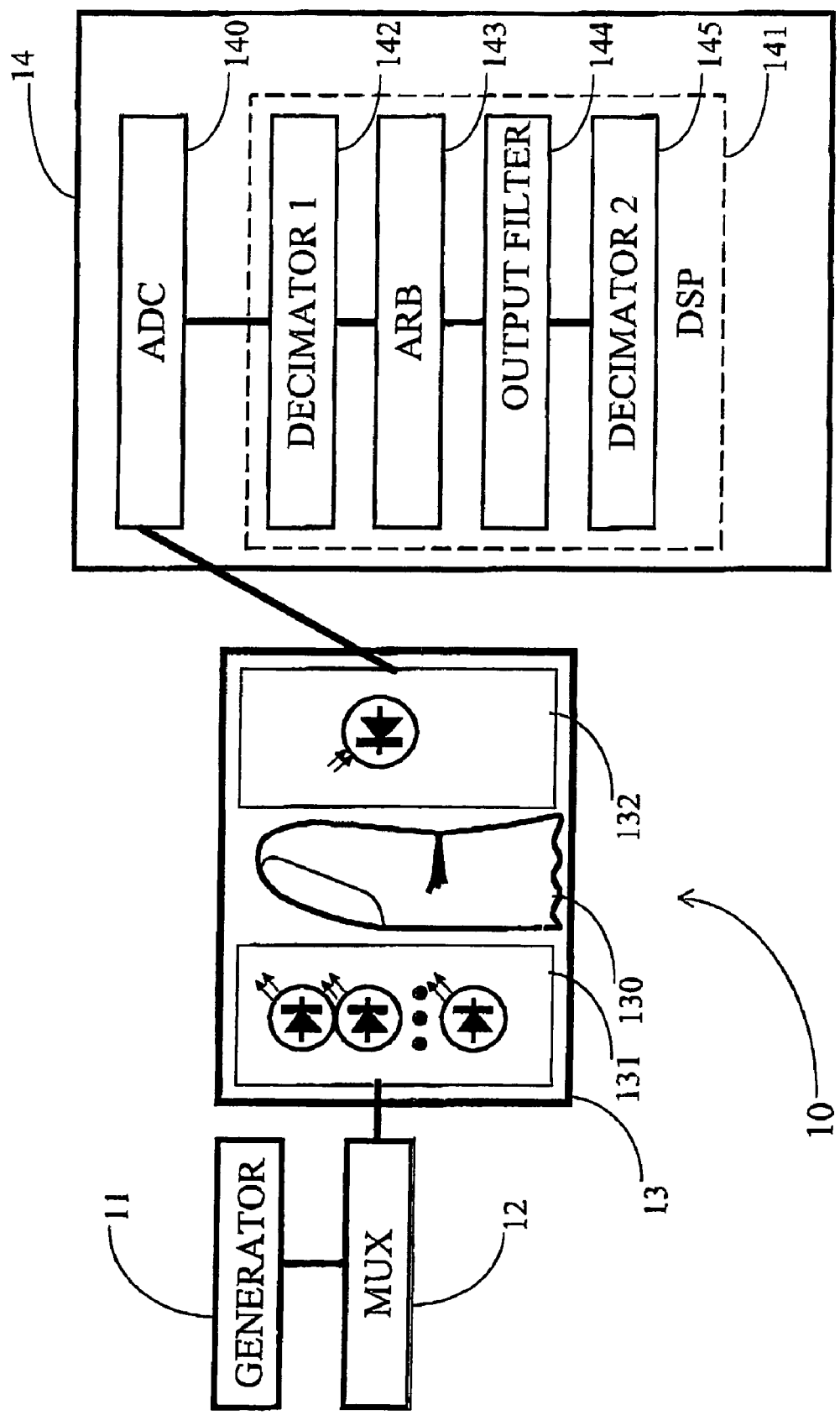
FIG. 1 is a schematic block diagram of a measuring system for the determination of blood parameters is illustrated, according to one embodiment of the invention.

The principles and operation of the process and system according to the present invention may be better understood with reference to the drawings and the accompanying description, wherein like reference numerals have been used throughout to designate identical elements. It is understood that these drawings are given for illustrative purposes only and are not meant to be limiting. It should be noted that the blocks in the drawings illustrating various embodiments of the system of the present invention are intended as functional entities only, such that the functional relationships between the entities are shown, rather than any physical connections and/or physical relationships.

Some portions of the detailed descriptions, which follow hereinbelow, are presented in terms of algorithms and symbolic representations of operations on data represented as physical quantities within registers and memories of a computer system. An algorithm is here conceived to be a sequence of steps requiring physical manipulations of physical quantities and leading to a desired result. Usually, although not necessarily, these quantities take the form of electrical or magnetic signals capable of being stored, transferred, combined, compared, and otherwise manipulated. In the present description, these signals will be referred to as values, elements, symbols, terms, numbers, or the like. Unless specifically stated otherwise, throughout the description, utilizing terms such as "processing" or "computing" or "calculating" or "determining" or the like, refer to the action and processes of a computer system, or similar electronic computing device, that manipulates and transforms data.

Referring to FIG. 1, a schematic block diagram of a measuring system 10 for determination of blood parameters is illustrated, according to one embodiment of the invention. The system includes a generator 11, a multiplexer (MUX) 12, a probe 13 and an analyzer 14 coupled to the probe 13. The generator 11 provides a series of pulses. These pulses are fed to the MUX 12, which is a switch configured to provide a composite operation mode regime of activation the probe 13.

The probe 13 comprises an illumination assembly 131 activated by the pulses generated by the generator and designed for generating light of different wavelengths (more than two different wavelengths). The probe 13 further includes a photodetector 132 adapted for sensing a light response of a blood perfused fleshy medium 130, and generating a multiple channel signal reflecting characteristics of the medium. Examples of the blood perfused fleshy medium include, but are not limited to, a patient's finger, a toe, a wrist, an elbow, etc. the illumination assembly 131 includes a plurality of light sources (e.g., LEDs), each associated with a wavelength selected in a range where the scattering properties of blood are sensitive to light radiation. When required, the illumination assembly 131 can be driven by a controllable drive mechanism that is not specifically shown. Examples of the photodetector 132 include, but are not limited to, spectrophotometers and/or photodiodes typically equipped with amplifying means, which are not specifically shown.

According to the invention, the MUX 12 is configured to provide a composite mode regime for ignition of the light sources. In other words, the light sources of the probe 13 can be run in the mode regime being different from the conventional pure parallel or serial mode regimes (described in the background section of the application). According to the invention, a mode regime representing a combination of parallel and short serial modes is employed, where pulses may have different rates. According to one embodiment of the invention, each LED is modulated over a short interval, e.g., over 1 to 5 on-off ignition cycles. This mode hereinafter will be referred to as a short serial mode regime (in contrast to the conventional serial mode regime in which each LED alternates over a considerably long interval, usually more than 10 on-off ignition cycles).

According to another embodiment of the invention, the LEDs can be divided into two or more groups, where each group is operated in the short serial mode, however, with a different rate. This mode regime hereinafter will be referred to as a short serial-parallel mode regime. According to this embodiment, the number of LEDs operating either in parallel or in series may be controllably adjusted. The duration of the LED's activity becomes a design parameter as well.

According to yet another embodiment of the invention, two or more pulse trains provided by the generator are initially mixed, thereby providing a single complex-frame signal, which is further applied to all the LEDs in a short serial-parallel mode regime. This mode regime hereinafter will be referred to as a mixed-rate short serial mode regime. According to this embodiment, each LED switches in a short serial mode by a triggering signal that represents a mixture of at least two generator waveforms of different rates.

The optical measurements are carried out to detect the light response of the medium (light transmitted through the medium or the light reflected therefrom, as the case may be), and to generate data representative thereof (constituting sensed signal).

The photodetector 132 of the probe 13 is coupled to the analyzer 14 responsive to the sensed signal. The multiple channel signal generated by the photodetector 132 is a composite signal including multiple sinusoids (having time-varying amplitudes) related to the LEDs' activity along with signal trends, disturbances and noise. The analyzer 14 is a computer device having an analog-to-digital converter (ADC) 140, a digital signal processor (DSP) 141 and a monitor (not shown) for presenting the measurement results. This analyzer 14 may be specially constructed for the required purposes, or it may comprise a general purpose computer selectively activated or reconfigured by a software program stored in computer's memory (not shown), such as, but is not limited to, any type of disk including floppy disks, optical disks, CD-ROMs, and magnetic-optical disks, read-only memories (ROMs), random access memories (RAMs), EPROMs, EEPROMs, magnetic or optical cards or any type of media suitable for storing electronic instructions, and each coupled to a computer system bus. The DSP 141 includes, a first decimator unit 142, an adaptive resonator bank unit 143, an output filter unit 144 and, optionally, a second decimator 145.

The ADC unit 140 is a known unit designed for sampling and digitizing the signal obtained from the photodetector 132. The first decimator 142 is configured for reducing the sampling rate of the digital signal treated in the DSP. The various examples of the decimating process utilized by the first decimator will be described below. The second decimator is designed for outputting the time evolutions of the light responses at a lower sampling rate (e.g., 25–30 sample/sec), which may be required for certain applications.

It should be appreciated that the DSP 141 is preprogrammed by a mathematical model capable of analyzing the received output (sensed signal) of the detection assembly and determining desired parameters of the patient's blood.

The adaptive resonator-bank (ARB) 143 constitutes of frequency-selective filters—resonators, configured for tracking and recovering the multiple time-varying sinusoids from the composite noisy signal generated by the photodetector 132. The ARB 143 concurrently performs the amplitude is demodulation for each channel along with frequency tracking and rejecting of the undesirable spectral lines, such as trends, disturbances and noise.

Finally, as a result of the operation of the output filtering unit 144, the light intensity signals associated with the LEDs' selected wavelength can be obtained and used for determining blood parameters by using an appropriate known method based on a relationship between these light intensities. For example, methods described in U.S. Pat. Nos. 6,400,972 and 6,587,704 assigned to the Applicant of this application, and incorporated herein by reference can be used for the determining of blood parameters.

According to the invention, the adaptive resonator bank (ARB) is based on the closed-loop resonator bank representing a parallel connection of narrow-band resonance filters with a feedback loop. The general mathematical principles of the application of the adaptive resonator bank (ARB) to the composite signal generated by the photodetector 132 will be expounded hereinbelow.

Generally, the composite signal generated by the photodetector 132 can be represented by a time-varying vector $s = s(n) = (\sigma_1, \ldots, \sigma_N)^T$, where $\sigma_i = A_i \cos(\omega_1 n + \Phi_i)$ is the i-th sinusoid having the amplitude $A_i$, the angular frequency $\omega_i$ and the phase $\phi_i$; n is the discrete time. For example, the composite signal can be represented by a sum of sinusoids corrupted by the noise $v = v(n)$, to wit, $y = \sigma_1 + \ldots + \sigma_N + v$. A retrieval of the sinusoids is usually performed by applying a filter bank that generates an N×1 output vector $y = (y_1, \ldots, y_N)$, where each component $y_i$ (i=1, ..., N) relates to the corresponding input element $\sigma_i$.

According to the invention, the determining of the vector $y = (y_1, \ldots, y_N)$ is carried out in terms of the state-space formulation of the Kalman-like spectral observer (see, for example, G. C. Goodwin, et al., "*Sinusoidal disturbance rejection with application to helicopter flight data estimation,*" *IEEE Trans. Acoustics, Speech, and Signal Processing*, 1986, V. 34(3), PP. 479–484), which for a single tone $\omega_i$ can be presented by the following closed-loop pattern:

$$x_i(n+1) = T_i x_i(n) + i\, G_i e(n),$$

$$e(n) = y(n) - h_i x_i(n) \qquad (1)$$

where $x_i = x_i(n) = [c_i\ s_i]^T$ is the 2×1 state vector comprising the in-phase and quadrature components $c_i$ and $s_i$, respectively; $G_i$ is the 2×1 gain vector; $h_i = [1\ 0]$ is the observation matrix, and $T_i$ is the 2×2 transition matrix $$T_i = \begin{bmatrix} C_i & S_i \\ -S_i & C_i \end{bmatrix} \qquad (2)$$

where $C_i = \cos(\omega_i)$ and $S_i = \sin(\omega_i)$, i=1, ..., N.

Accordingly, the N-sinusoid Spectral Observer can be represented by $$x(n+1)=Tx(n)+Ge(n),$$

$$e(n)=y(n)-hx(n) \qquad (3)$$

where $x=x(n)=[x_1, \ldots, x_N]^T$; $G=[G_1, \ldots, G_N]^T$; $h=[h_1, \ldots, h_N]$, and the 2N×2N transition matrix is defined as T=block diag$\{T_i\}$, i=1, ..., N.

The transfer function (TF) connecting the prediction error e with the particular i-th output $x_i$, $F_i(z):e \to x_i$, corresponding to the i-th sinusoid can be obtained by $$F_i = \begin{bmatrix} z-C_i & -S_i \\ S_i & z-C_i \end{bmatrix}^{-1} \quad G_i = \frac{1}{1-2C_iz^{-1}+z^{-2}} \begin{bmatrix} z-C_i & S_i \\ -S_i & z-C_i \end{bmatrix}, \qquad (4)$$

where z is the forward time-shift operator.

For example, in the case when the gain is represented by $G_i = \gamma g_i = \gamma[C_i, -S_i]^T$, where $\gamma$ is the relaxation factor, the corresponding mathematical model yields the following expression for the i-th sinusoid TF:

$$F_i = \frac{\gamma}{z^2 - 2C_iz + 1} \begin{bmatrix} C_iz-1 \\ -S_iz \end{bmatrix} \qquad (5)$$

As can be appreciated the numerator of the fraction in Eq. (5) matches the corresponding sinusoidal oscillator. In other words, each particular component of the processed optical signal is associated with the corresponding resonator in the ARB. It should be noted that the entire closed-loop pattern of the multi-sinusoid spectral observer is identical to the known in the art closed-loop resonator bank (CLRB) configuration, that is known per se (see, for example, N. Chernoguz, "*Tracking and recovering multiple sinusoids by an adaptive resonator bank,*" Proc. Fourth IASTED International Conference Signal and Image Processing, 2002, PP. 49–54).

Figures 2, 3:
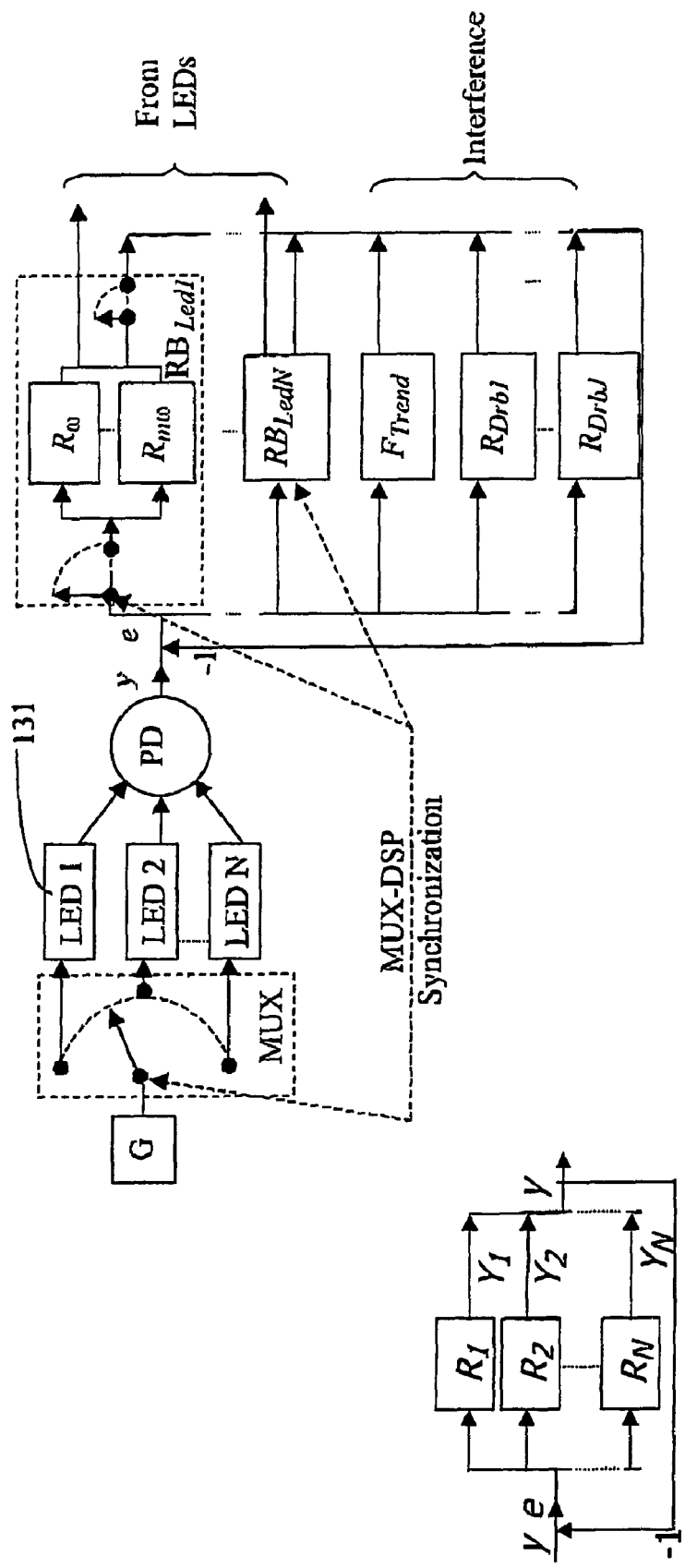
FIG. 2 is a schematic block diagram illustrating the closed-loop resonator bank configuration.
FIG. 3 is a schematic block diagram illustrating a synchronization between the light sources and resonators in the system of the present invention.

FIG. 2 illustrates a block-diagram of the CLRB configuration. In the mathematical model corresponding to the CLRB configuration, the i-th resonator $R_i$ can be represented by $$R_i = \gamma \frac{C_iz^{-1} - z^{-2}}{1-2C_iz^{-1}+z^{-2}} \qquad (6)$$

In turn, the transfer function $\Phi_i: y \to y_i$, connecting the total input with the particular i-th output $y_i$ (or, equivalently, $c_i$) can be obtained by $$\Phi_i = R_i \bigg/ \left(1 + \sum_{j=1}^{N} R_j\right) \qquad (7)$$

It should be appreciated that when the frequency of the transfer function (TF) achieves the location of the corresponding resonant peak, then the other resonators in the denominator may be ignored, and the magnitude of the TFP $\Phi_1$ for the corresponding sinusoid tends to 1.

It should be relevant to note here that in the single tone case (i.e., when N=1), the above multi-tone decomposition scheme reduces to a trivial zero-phase bandpass filter (BPF), where the corresponding transfer function $W_i$ can be obtained by $$W_i = \gamma \frac{C_iz^{-1} - z^{-2}}{1 - 2(1-0.5\gamma)C_iz^{-1} + (1-\gamma)z^{-2}} \qquad (8)$$

It should be also noted that since the N-sinusoid spectral observer represented by the system of equations (3) describes the propagation of both the in-phase and quadrature components, then the desired amplitude and phase of all the N sinusoids can be calculated. In particular, the corresponding quadrature TF of the i-th sinusoid can be obtained by $$Q_i = -\gamma \frac{S_iz^{-1}}{1-2C_iz^{-1}+z^{-2}} \qquad (9)$$

Moreover, by utilizing the in-phase and quadrature components $c_i$ and $s_i$, respectively, the amplitude and phase of corresponding i-th sinusoid can be obtained by $$A_i = \sqrt{c_i^2 + s_i^2}. \qquad (10a)$$

and $$\phi_i = utun(c_i/s_i). \qquad (10b)$$

In order to take into account the fact that signal generated by the photodetector can be corrupted by optical disturbances and/or signal trends, the auxiliary states have to be included into the mathematical model described above for each disturbance and/or trend. Thus, a single-component bias term $x_{Bias}$ has to be added to the mathematical model described above for the trend. In such a case, the one-state equation $$x_{Bias}(n+1) = T_{Bias} x_{Bias}(n) + G_{Bias} e(n) \qquad (11a)$$

should be added to the N-sinusoid spectral observer represented by the system of equations (3) with the identity transition function $T_{Bias}=1$ and gain $G_{Bias}$. Here, the filter gain can be factored by a relaxation parameter $G_{Bias}=\epsilon$ appropriate for the trend change. The observation function h can be updated by the component $h_{Bias}=1$.

Likewise, a Nyquist single-state term $x_{Nqst}$ corresponding to the Nyquist noise component can be taken into account. In this case, the one-state equation $$x_{Nqst}(n+1) = T_{Nqst} x_{Nqst}(n) + G_{Nqst} e(n) \qquad (11b)$$

should be added to the N-sinusoid spectral observer represented by the system of equations (3) with the transition function $T_{Nqst}=-1$, and the gain $G_{Nqst}$. The Nyquist gain has a negative sign and can be factored by a relaxation parameter $\gamma$, so that $G_{Bias}=-\gamma$. The observation function h can be updated by the component $h_{Nqst}=1$.

It should be noted that in the presence of periodic noise components, the N-sinusoid spectral observer should be updated by the proper resonators in the form of Equation (1) based on the knowledge of the noise component spectra.

In the case when the central resonator frequency is unknown, the stationary CLRB version described above can be updated, in order to enable the estimation of the frequency-related parameter. For example, the adjustment of the frequency can be carried out by computing the phase increment over the one-step update, namely $$\phi_i(n)=\rho\omega_i(n-1)+(1-\rho)[\phi_i(n)-\phi_i(n-1)] \quad (12)$$

where $\phi_i(n)$ is the phase computed in accordance with Eq. (10b), and properly unwrapped, when required; and $\rho$ is a relaxation factor which is a tuning parameter. The unwrapping of the phase assumes complementing the phase, when it jumps higher than $\pi$ radian, so that the phase argument would maintain its continuity. The frequency adjustment translates the CLRB configuration into an adaptive resonator bank (ARB) form.

Figure 4:
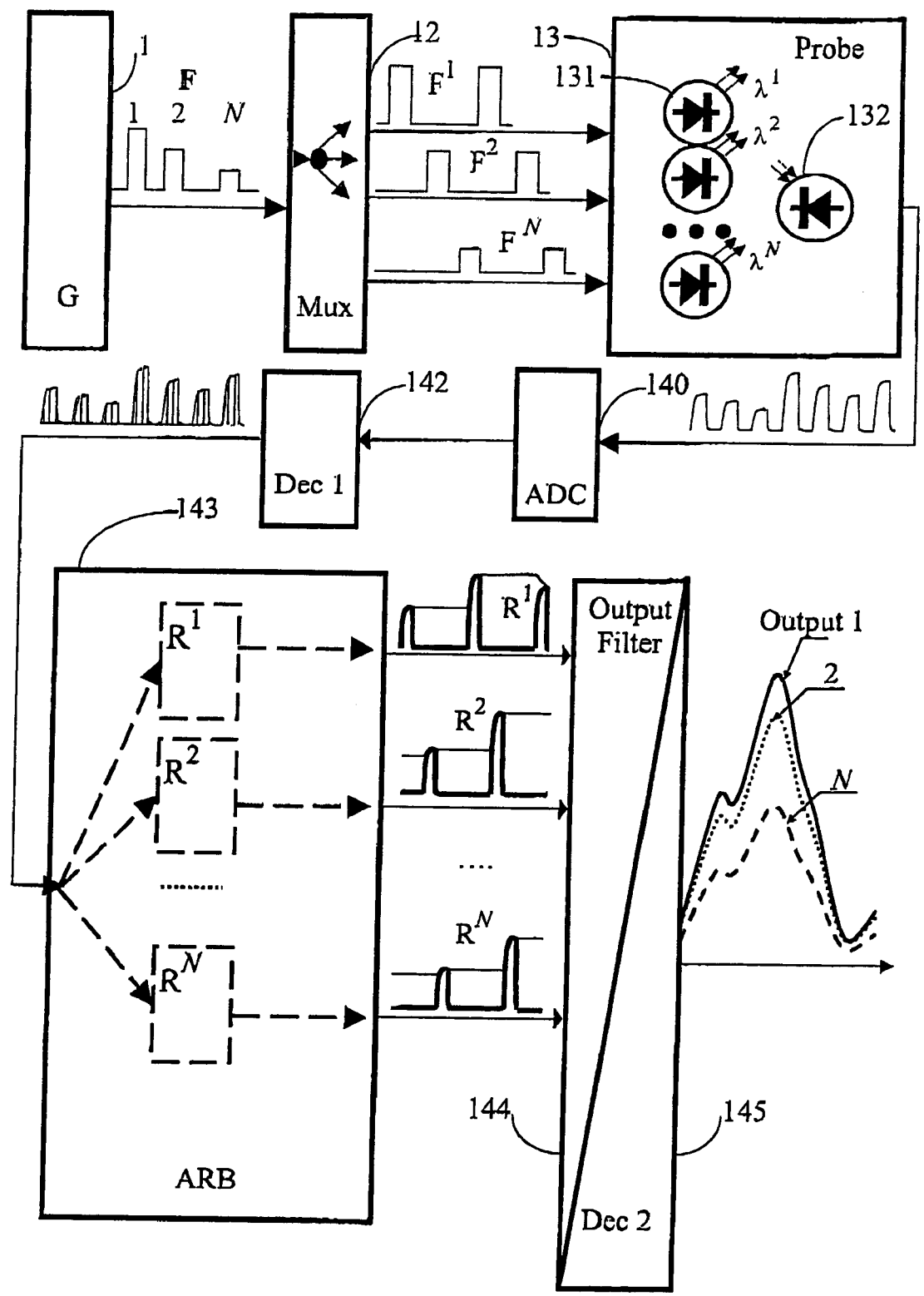
FIG. 4 is a schematic block diagram of a system of the present invention operating in a short serial mode regime, according to one example of the invention.

Referring to FIG. 4, main units of the system of the present invention is illustrated, according to another embodiment of the invention. According to this embodiment, a synchronization is provided between the illumination assembly 131 and the adaptive resonator bank (ARB) 143 operating in one of the regimes selected from a short serial mode, short serial-parallel mode and mixed-rate short-serial mode regimes.

In operation, each light source (hereinafter all types of the possible light sources for conciseness will be referred to as LEDs) of the illumination assembly 131 turns on and off at a presumed rate producing periodic, nearly square probe optical waveforms. The total light signal (transmitted, scattered or reflected) is sensed by the photodetector 132. The multiple channel signal generated by the photodetector 132 is fed to the analyzer where it (after conditioning and amplification) is sampled, e.g., at the rate of about 250–300 kHz, and thereafter decimated. According to the invention, the signal after the sampling and decimating is treated by the DSP 141 in a multi-stage signal processing representing a particular demodulation-decimation technique. Examples of the demodulation-decimation will be described below in detail.

As describe above, according to one embodiment of the invention, LEDs can generally operate in a short serial-parallel mode regime. In this regime, all the LEDs are divided into several parallel groups, each associated with a particular modulation rate. In each group LEDs are involved in a short serial mode, one by one, for a short interval comprising one (or few) cycles of ignition. The number of the parallel groups, rates and intervals of the LED activity are design parameters, which should be adjusted in accordance with the system requirements.

Alternatively, according to another embodiment of the invention, LEDs can generally operate in a mixed-rate short serial mode regime. In this regime, two or more generator-induced sequences with different modulation rates are initially mixed, and then the aggregated pulse train is fed to each LED in the short serial mode regime.

According to one embodiment of the invention, the ARB can reserve one particular resonator for each corresponding LED (i.e., wavelength). In other words, only fundamental harmonics are extracted from the composite signal. Thus, for given N LEDs (i.e., N optic channels), N corresponding resonators are to be involved, according to this embodiment. In such a case, the resonant frequency of each resonator fits the modulation rate of the corresponding LED. It should be noted that when the LEDs are activated concurrently, in a parallel mode, their frequencies should be different, while when the LEDs are activated serially, the modulation rate for all LEDs may be identical.

It should be appreciated that when required, several resonators ($R_\omega$ through $R_{m\omega}$) can be used for each optic channel, corresponding to different harmonics associated with this channel (see FIG. 3).

As shown in FIG. 3, the synchronization between the MUX and the ARB is provided. For example, when a particular LED is turned on, the input composite signal is fed to the appropriate resonator, and the resonator's output is linked to the total output signal. In turn, when a particular LED is turned down, the corresponding resonator's input is locked and the resonator's output does not contribute into the total output. However, the resonator with the locked input can sustain oscillations in the autonomous mode, in order to be synchronized in time with all the input components. Hence, the resonator can produce a contemporary signal, irrespective of the LED's activity.

According to the invention, the adaptive resonator bank can be further designed to handle slowly varying components of the composite signal provided by the photodetector 132, e.g., signal trends. The signal trends are usually described by its first derivatives, e.g., the dc (constant component), slope (rate). Optionally, the signal trends can be described by higher signal derivatives, e.g., acceleration and jerk. A corresponding portion of the ARB responsible for handling the trends is referred to as a trend filter. According to the invention, the trend filter is attached to the CLRB configuration (see Eq. (11a)) with the corresponding trend filter $F_{Trend}$ for the signal trend.

It should be noted that the number of the derivatives used in the trend filter depends on the trend's order. For instance, because in practice the dc is the most dominant component, the appropriate trend filter has the first order. In turn, the trend filter, relying on the dc component and the slope, can have the second order, etc. Hence, the trend filter has a predetermined order and is capable to track the signal trends, irrespectively of the LED's modulation node.

Likewise, a further portion of the resonators attached to the CLRB configuration can be responsible for the rejection of different periodic disturbances having either known or unknown frequencies. Such resonators can have predetermined in advance resonant frequencies, when the interference location in the frequency domain is known. When the frequencies are unknown, the frequencies can be properly adjusted, for example by using the scheme described by Eq. (12). Thus, the application of the CLRB configuration (represented by the spectral observer scheme) enables to eliminate various narrow-band disturbances from the input composite signal, and therefore prevents their influence on the LED-related components. In the same manner, resonance filters, related to other types of interference, may also be introduced into the ARB framework.

It should be relevant to emphasize here that instead of eliminating various narrow-band disturbances from the composite input signal by applying a notch filter before deriving LED's related signals, the present invention teaches to eliminate the interference spectral components simultaneously with the recovering of desired components. This processing scheme is common for the LED's related signals as well as for the trends, disturbances and noise. According to the invention, the elimination of the trends, disturbances and noise is carried out by applying a corresponding APB. Such an approach provides an accurate separation of the desired channels from the undesired spectral components, whereas a "bandstop" rejection of the undesired disturbances by the notch filtering before the decomposition of the LED's induced signals may affect the desired spectral components as well.

For example, the signal processing by the ARB shown in FIG. 3 can be formulated as follows. The treated signal y(t)

can be represented as a superposition of induced by LEDs' periodic multiple-harmonic signals, slow trend signal, sinusoidal or periodic disturbances, and a noise.

In a general scenario, the LEDs can be driven by the r pulse trains having different pulse rates $\omega_r$, r=1, 2, . . . The l-th LED is activated by the-corresponding l-th portion of the pulse train (if the train sequence is single) or by a superposition of the l-th portion in each r-th train (if several triggering train sequences are applied at a moment of time). In such a case, the corresponding composite signal provided by the photodetector can be presented by:

$$y(t) = \sum_{l=1}^{N} \sum_{r=1,2...} \sum_{k=1,3...} \chi_r^l A_{r,l,k} \sin(k\omega_r i + \varphi_i) + \sum_{j=1}^{J} D_j \sin(\omega_j t + \varphi_j) + Trend(t) + v(t)$$ (13)

The first sum-term in the right-hand side of Eq. (13) represents a sum of the LED-related waveforms over (i) N LEDs, (ii) fundamental to higher harmonics associated with particular pulse sequence waveform, and (iii) all the driving pulse sequences involved. The second sum-term relates to the sum of sinusoidal disturbances. The next term, denoted as Trend, refers to a slow time-varying trend, while the last term designates the white noise.

The link between the LED activity and resonators is established via the LED switch function $\chi_r^l$. The factor $\chi_r^l = \chi_r^l(t)$ is the binary (0/1) function that equals 1, when the l-th LED is activated by the r-th pulse train; or 0, otherwise. In this notation, the superscript indicates the l-th pulse position in the pulse train driving the l-th LED. As the LEDs are driven by a single pulse sequence, i.e., r=1, the subscript r in the LED switch function may be omitted, resulting in a reduced notation $\chi^l = \chi^l(t)$, where l denotes the LED, l=1, . . . , N. As the number of pulse sequences involved is more than 1, the LED switch function obtains a subscript r, r=1, 2, . . . denoting the driving sequence.

For treating the signal described by Eq. (13), for example, the Kalman-like spectral observer (SO) scheme, described above, with "nearly" optimal gain can be employed. Such a modified SO scheme takes into account that the particular p-th resonator for a single tone $\omega_r$ can be involved only at particular instants of the LEDs' activity indicated by the binary (0/1) switching function $\chi_r^l$; to wit:

$$x_p(n+1) = T_p x_p(n) + \chi_r^l(n) G_p e(n)$$ (14)

In other words, the prediction step in Eq. (14) is completed as usual (see Eq.(1)), while the update step is controlled by the LED's switching function $\chi_r^l$.

Likewise, the spectral observer is a generalization of the single-tone version, to wit:

$$x(n+1) = Tx(n) + \chi(n) G e(n),$$

$$e(n) = y(n) - \chi(n) h x(n)$$ (15)

where $\chi(n)$ should be properly composed from the binary switching functions $\chi_r^l(n)$, r=1, 2, . . . ; l=1, . . . , N. An example of the detailed description of the switching function $\chi(n)$ will be given below. It is relevant to note here that the computation the prediction error also depends on the function $\chi(n)$ and should be in agreement with the resonators states. Further, it is found convenient to aggregate the functions $\chi(n)$ and h into a resulting observation function h(n) composed of the particular LED's switching functions $\chi_r^l(n)$.

It should be appreciated by a person versed in the art that the state vector x should, minimally, comprise the states associated with the LEDs' in-phase and quadrature components. In a more general consideration, when periodic interference (optical and/or electromagnetic) disturbs the signal, the corresponding auxiliary states should be involved into the model.

For example, an electrical interference at a fixed frequency (e.g., 100 Hz) may affect the PD signal. This continuous-time interference may appear irrespective of the LEDs' control mode. Hence, the resonator operating at the corresponding frequency of 100 Hz should be included into the SO scheme with corresponding switching function, that is always equal to 1.

Moreover, when the value of the frequency is unknown (or slightly varies with time), a frequency estimator can be applied, e.g., based on Eq. (12). For this purpose, the corresponding frequency estimator can be updated recursively, as indicated above.

Further, three examples of the configuration system of the present invention will be illustrated.

EXAMPLE 1

Figure 5:
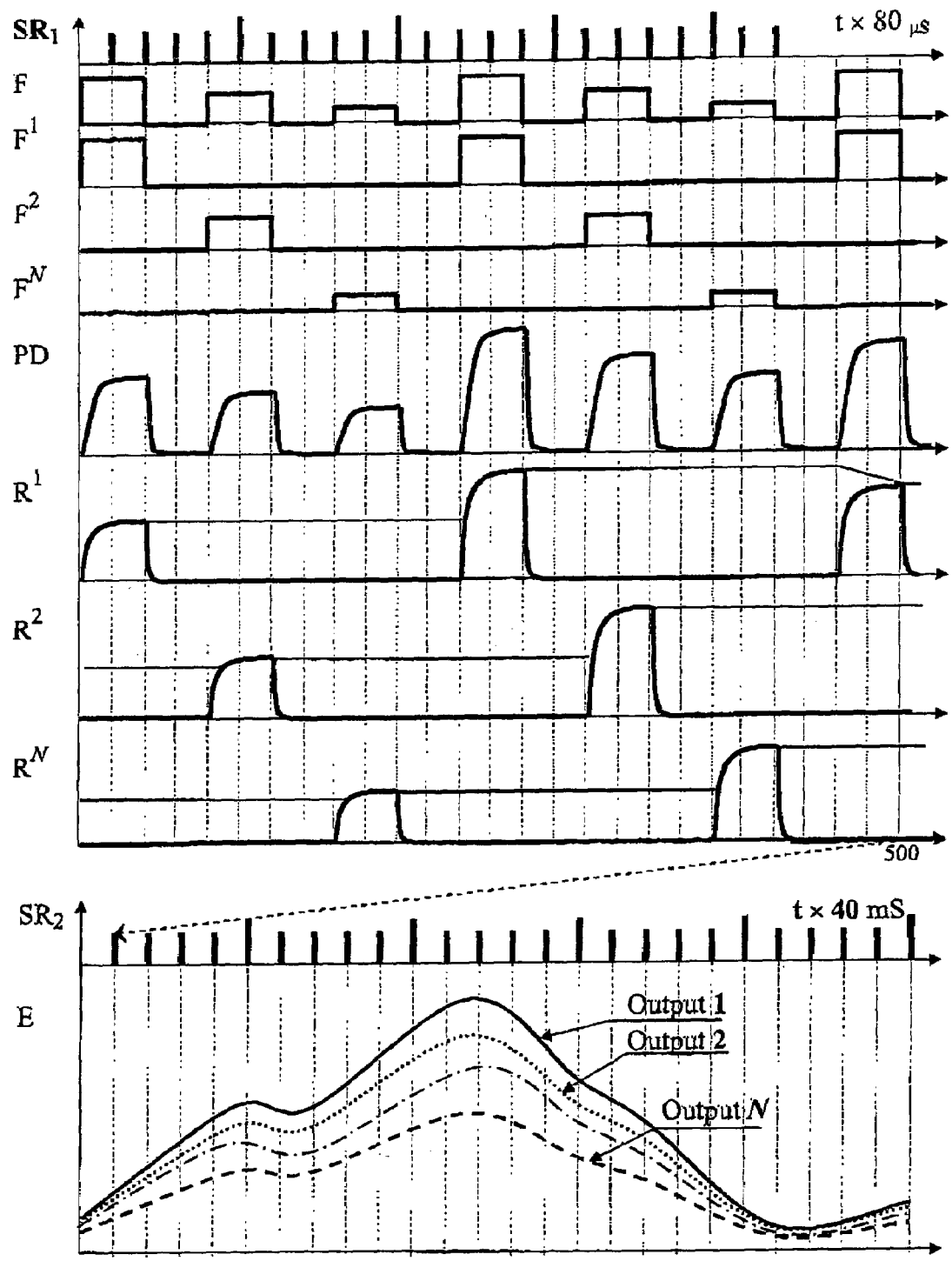
FIG. 5 illustrates an example of waveforms produced by different elements of the system shown in FIG. 4.

FIG. 4 illustrates a schematic diagram of a system operating in a short serial mode regime. According to the invention, the MUX 12 is configured to operate in a short serial mode regime. FIG. 5 illustrates an example of waveforms produced by different elements of the system shown in FIG. 4.

According to this example, a series of activating pulses F (provided by the generator 11) are fed to the MUX 12. The MUX 12 operates in such a manner that only one on-off ignition cycle is provided for the modulation of each light source 131. The pulses $F^1, F^2, \ldots$ and $F^N$ correspond to the operation regime of the light sources having numbers 1, 2, . . . and N, respectively. Hence, the light sources are run in series, one after another, each LED over one ignition circle. Further, the pulses indicated by symbol PD correspond to the composite signal generated by the photodetector 132 in response to the light provided by the light sources 131 activated by the pulses $F^1, F^2, \ldots$ and $F^N$. The analog signal PD, converted by he ADC 140 into a high-sample-rate digital signal, and resampled by the first decimator 142 to a lower rate $SR_1$, is then decomposed by the ARB 143 which produces a set of pulses associated with resonators $R^1, R^2, \ldots$ and $R^N$, corresponding to the light sources having the numbers 1, 2, . . . , N, respectively. Finally, the pulses can be filtered out and the output signals 1, 2, . . . , N representing light intensity E corresponding to the light sources having the numbers 1, 2, . . . , N, respectively, can be obtained and used for determination of blood parameters.

For instance, when a number of the light sources equals 10, a sampling rate of 250 kHz can be used for sampling the signal PD generated by the photodetector. Preferably, the modulation frequency for the activation of the light sources (e.g., LEDs) is synchronized with the operation of the ARS. Thus, the light modulation frequency can be selected within a wide range restricted from the high frequency limit by the system's time constant, and from the low frequency limit by the low frequency disturbances and their most essential harmonics. In the short serial regime of this above example, each LED can be turned on over 40 samples, and turned off over next 40 samples. Hence, the LED's ignition period is 80 samples, which is equivalent to the modulation rate 250/80=3.125 kHz.

It should be noted that although triggering the light sources provides nearly ideal square pulses (see the pulses $F^1$, $F^2$, . . . and $F^N$), the signal produced by the photodetector (that is usually integrated with an amplifier) represents a periodic signal with a rather complex shape and, accordingly, with a wide harmonic content. Thus, a decimation step should avoid the aliasing phenomenon, i.e., a leakage of the higher-order harmonics into the lower frequencies.

It should be relevant to note here that the length of conventional anti-aliasing low-pass filters is usually several (e.g., 3–4) times higher than the decimation ratio and this may cause undesired coupling between the LEDs. Therefore, the decimation performed with the help of a conventional anti-aliasing filter is not appropriate here, due to the strong necessity to keep independence between the different LEDs. Nevertheless, the method of the present invention allows to reduce the 250 kHz sampling rate by avoiding the aforementioned straightforward decimation procedure. The reduction can be done by relying on the particular spectral content of the given signal.

More specifically, noting that the generated signal is nearly an ideal symmetric waveform, the odd harmonics of the spectrum can only be taken into account, while the even harmonics, describing the pulse asymmetry, can be ignored. By integrating consequent groups of the samples, it is possible to reduce the sampling rate and narrow the spectrum bandwidth, by keeping in mind the location of the desired odd and undesired even harmonics in the frequency domain.

In particular, one should take into account that the high-order odd harmonics can merge, after the decimation, with the lower odd harmonics, while high-order even harmonics can merge with the lower even harmonics. Thus, by using the two-sample summation, the sampling rate can be reduced to 125 kHz. In such a case, the even 80-th harmonic merges with the dc, the 79-th harmonic merges with the 1-st (fundamental) harmonic, etc. Therefore, after the two-sample summation stage, the only 40 harmonics remain. Likewise, the summation of several samples, may result in the situation when only few lower harmonics remain in the compressed spectrum. Thus, only small number of resonators can be required for each channel. For instance, the summation by 10 samples results in a spectrum comprising only 1-st and 3-rd harmonics. In other words, only two resonators are required for each channel.

Accordingly, the summation by 20 samples results in such a situation, in which all the odd harmonics would merge with the 1-st harmonic at 3.125 kHz. In turn, the even harmonics would partially merge with the dc component, and partially with the Nyquist frequency, e.g., 6.25 kHz. This approach provides a spectrum with a single odd harmonic, which needs only a single resonator.

Thus, the summation by 20 samples reduces the original sampling rate of 250 kHz to the rate $SR_1$ of 12.5 kHz (see FIG. 5). Accordingly, the integrated sequence of pulses contains a 2-sample on-portion and a 2-sample off-portion. Hence, the total sample rate of the sequence is set to 3.125 kHz, i.e., 4 samples per one on-off ignition cycle. Accordingly, the basic frequency of 3.125 Hz can merge with all the odd harmonics presented in the original (6.125 kHz width) spectrum, i.e., with the harmonics corresponding to 3.125× (3, 5, . . . , 39) kHz. In turn, the 40-th harmonic falls onto the dc component, the 38-st—onto 6.25 kHz (Nyquist), the 36-st—onto the dc, the 34-st—onto the Nyquist signal, etc. As noted above, only the odd harmonics are taken into account, while the even harmonics are ignored. Hence, the resonator should match the 3.125 kHz, while the dc and Nyquist components may be rejected.

According to the invention, the MUX distributes the pulse sequence between the different LEDs. Accordingly, the 1-st LED receives the first pulse of the sequence, the 2-nd LED receives the second pulse, etc. (see, for example, the pulses $F^I$, I=1, 2, . . . , N shown in FIG. 5). Hence, each LED, in turn, can be switched on and off over a period of 4 samples (at the 12.5 kHz rate), and then would remain passive over the next 9×4=32 samples. The minimal shift between the consequent active LEDs is 4 samples.

The photodetector integrates the optical signals induced by all N LEDs and generates the composite signal (PD in FIG. 5). As can be seen from the shape of the PD signal, the square-waveform of the original LED's pulses $F^I$ is slightly disturbed by the PID inertia. It should be noted that the particular pulse frequency of 3.125 kHz can be selected to provide a minimal leakage between the consequent LEDs' waveforms.

The signal PD is fed to the ARB for filtering and channel separation. The ARB corresponding to this example can comprise at least N (e.g. N=10, as in the present example) resonators having identical fundamental frequency 3.125 kHz, and producing $R^1$, $R^2$, . . . , $R^N$ signals. All these resonators operate in parallel, however at each moment the PD signal is fed to only one of them, owing to the LED switch functions $\chi^1$, . . . , $\chi^N$, which are binary 1 or 0 indicators synchronizing the ARB with the LEDs' operation. Hence, for the given 10 wavelengths, the state vector of the spectral observer comprises 20 states (one in-phase and one quadrature for each resonator), where two parameters in the state-space vector are reserved for the dc component (0 Hz) and the Nyquist frequency (6.25 kHz), respectively.

Each output of resonators represents a periodic signal having a certain amplitude. The shape of the signals $R^1$, $R^2$, . . . , $R^N$ can be different from the square waveform of the original LED's pulses $F^k$. It should be appreciated that when required, the original pulse form can be reconstructed with the help of auxiliary resonators related to higher harmonics.

At the last stage, when required, the 12.5 kHz sampling rate can be further reduced by using a conventional decimation, e.g., to the 25 Hz sampling rate, where all the channels would indicate the time evolutions of the light responses synchronously.

EXAMPLE 2

Figure 6:
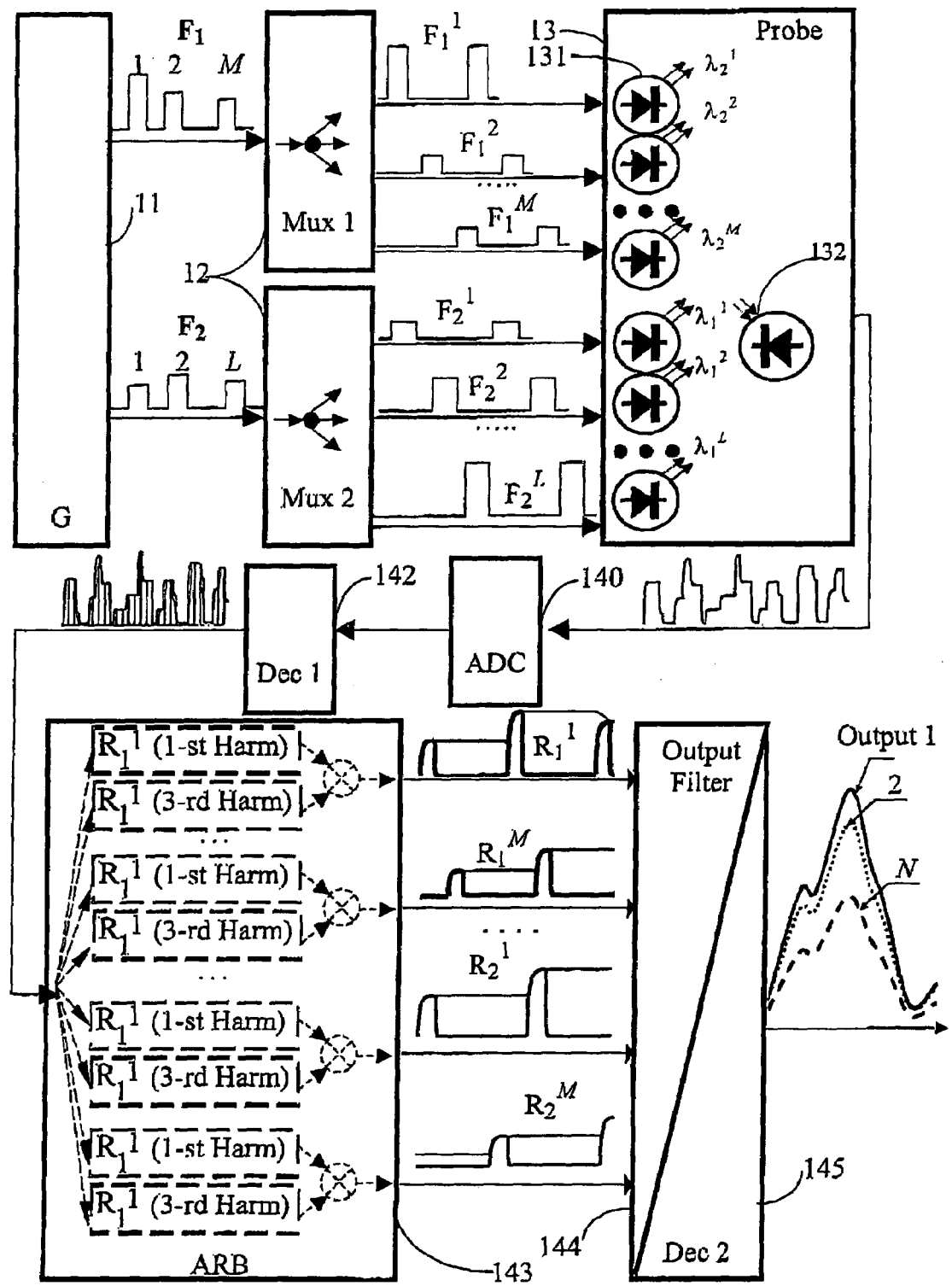
FIG. 6 is a schematic block diagram of a system of the present invention operating in a short serial-parallel mode regime, according to another example of the invention.
Figure 7:
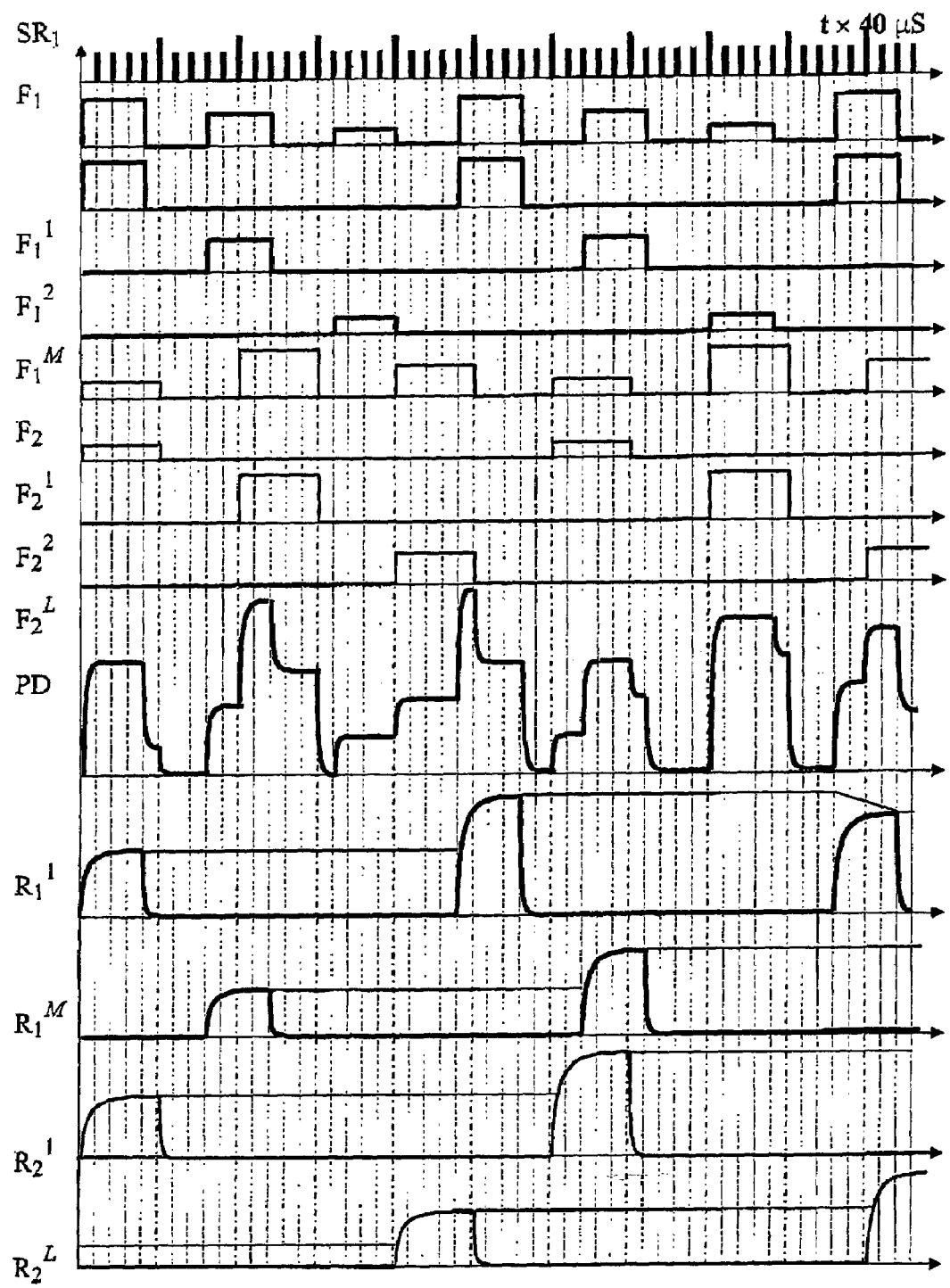
FIG. 7 illustrates an example of waveforms produced by different elements of the system shown in FIG. 6.

Referring to FIG. 6 and FIG. 7 together, an example of the system operating in a short serial-parallel regime and the corresponding waveforms are illustrated. The system of this design is different from that described in Example 1 in that the ten LEDs are divided into two parallel groups. The number of the LEDs in each group may be arbitrary, e.g., 6 and 4, or 9 and 1, or 5 and 5, etc. The first group comprises the LEDs $\lambda_1^1$ through $\lambda_1^M$, and the second group comprises the LEDs $\lambda_2^1$ through $\lambda_2^L$, where M+L=10. The first and second groups are fed by MUX1 and MUX2, respectively, and operate in the short serial mode each, how ever at different rates. For example, the rate of 3.125 kHz for the first group and the rate of 2.5 kHz for the second can be selected.

Accordingly, the Generator 11 outputs two pulse sequences $F_1$ and $F_2$ shown in FIG. 7. Contrary to Example 1, in the present example the 250 kHz samples are integrated by groups of 10 samples, thus reducing the sample rate from 250 kHz to 25 kHz. Thus, in the first sequence each activating pulse contains 8 samples per on-off cycle (4 samples for the on-portion and 4 samples for the off-portion), while each pulse in the second sequence contains 10 samples per on-off cycle (5 samples for the on-portion and 5 samples for the off-portion). It should be noted that owing to the sampling rate of 25 kHz, the signal spectrum bandwidth is 12.5 kHz, i.e. half of the sampling rate.

To this end, the spectrum having the width of 12.5 kHz can exhibit only the 1-st and 3-rd (9.375 kHz) harmonics of the first, i.e., the 3.125 kHz rate sequence. With regard to the second, i.e., the 2.5 kHz rate sequence, the situation is similar. The 5-th harmonic of the fundamental frequency of 2.5 kHz (i.e., 12.5 kHz) can merge with the Nyquist frequency and should be disregarded. Therefore, only the 1-st and 3-rd harmonics (7.5 kHz) of the fundamental frequency of 2.5 kHz can be used. Note that using the 3-rd harmonic can increase the system bandwidth, when compared to the previous example. Thus, two resonators should be reserved for each LED in the corresponding ARB. In this case, the total LED output is obtained by aggregating the 1-st and 3-rd harmonics.

Accordingly, the pulses from the first sequence $F_1$ are fed to the corresponding LEDs in the first group. In particular, the subsequence $F_1^1$ drives the LED $\lambda_1^1$, the subsequence $F^{12}$ drives the LED $\lambda_1^2$, etc. In turn, the pulses of the second sequence $F_2$ are fed to the second group of the LEDs. In particular, the subsequence $F_2^1$ drives the LED $\lambda_2^1$, subsequence $F_2^2$ drives the LED $\lambda_1^2$, etc. It is relevant to recall that in the notations used here the subscript indicates the Generator sequence (in particular, the first or second), while the superscript—the pulse in the sequence (1 to N).

The signal PD in FIG. 7 represents an output waveform generated by the photodetector in response to the signals induced by the LEDs. The signal PD is then decomposed by the ARB 143. According to this example, the resonators of the ARB operate in a mixed time-frequency separation mode. Thus, the resonators associated with the 1-st group of the LEDs operate in series. A part of these resonators is synchronous with the basic frequency 3.125 kHz, and a remaining part is synchronous with its 3-rd harmonic having the frequency of 9.375 kHz.

More specifically, each LED is associated with two resonators or, in other words, with two pairs of states in the spectral observer state vector, wherein a first pair (in-phase and quadrature) corresponds to the 1-st harmonic and a second pair corresponds to the 3-rd harmonic. The spectral observer state vector comprises, therefore, 40 states for 10 wavelengths.

For instance, a two-component state vector $x_i$ can relate to the in-phase and quadrature of the 1-st harmonic of the 1-st LED. The corresponding resonator is specified by (i) the appropriate LED switch function $\chi_1^1$ (related to the 1-st sequence and 1-st pulse position in the 1-st sequence) and (ii) the appropriate gain and transition matrix (matching the rate 3.125 kHz). Accordingly, a two-component state vector $x_{i+1}$ can relate to the in-phase and quadrature of the 3-rd harmonic of the 1-st LED and the same switch function $\chi_1^1$, while the gain and transition matrix should be in agreement with the tripled modulation rate 9.375 kHz. Likewise, the next two states (four components) are associated with the 1-st and 3-rd harmonics of the 2-nd LED synchronized by the switch function $\chi_1^2$, and the same for all M LEDs of the first group of LEDs.

For the L LEDs of the second group, the resonators should be in agreement with the modulation rate of 2.5 kHz and its 3-rd harmonic. It should be appreciated that the corresponding modification can also affect the elements of the SO transition matrix T and the gain vector G. The resonators of the second group are synchronized with second sequence of pulses through the LED switch functions $\chi_2^1, \ldots, \chi_2^L$.

Another difference of Example 2 from Example 1 is in that the output of the resonators is obtained by aggregating the 1-st and 3-rd harmonics related to the same LED. Accordingly, the algorithm should contain a step representing the aggregation of the resonators corresponding to different harmonics of the same LED signal.

Turning back to FIG. 7, examples of the outputs of the ARB obtained by the aggregation of the 1-st and the 3-rd harmonics are depicted. In particular, $R_1^1$ is associated with the LED $\lambda_1^1$, an output $R_2^1$ is associated with the LED $\lambda_2^1$, etc.

It should be noted that when the mixed serial-parallel mode regime is employed, the LEDs' silence intervals become smaller than in the pure serial mode regime of Example 1, thus the smoothing ability and the bandwidth of the system are improved. Moreover, the modulation rates 2.5 Hz and 3.125 kHz are set sufficiently far from each other, thus preventing the coupling between the LEDs.

The number of the LEDs in the parallel groups may be arbitrary selected to meet the system requirements. For example, one particular LED, providing a reference wavelength, may be operated continuously at the modulation rate of 2.5 kHz, while the other 9 LEDs may operate in a short serial mode.

EXAMPLE 3

Figure 8:
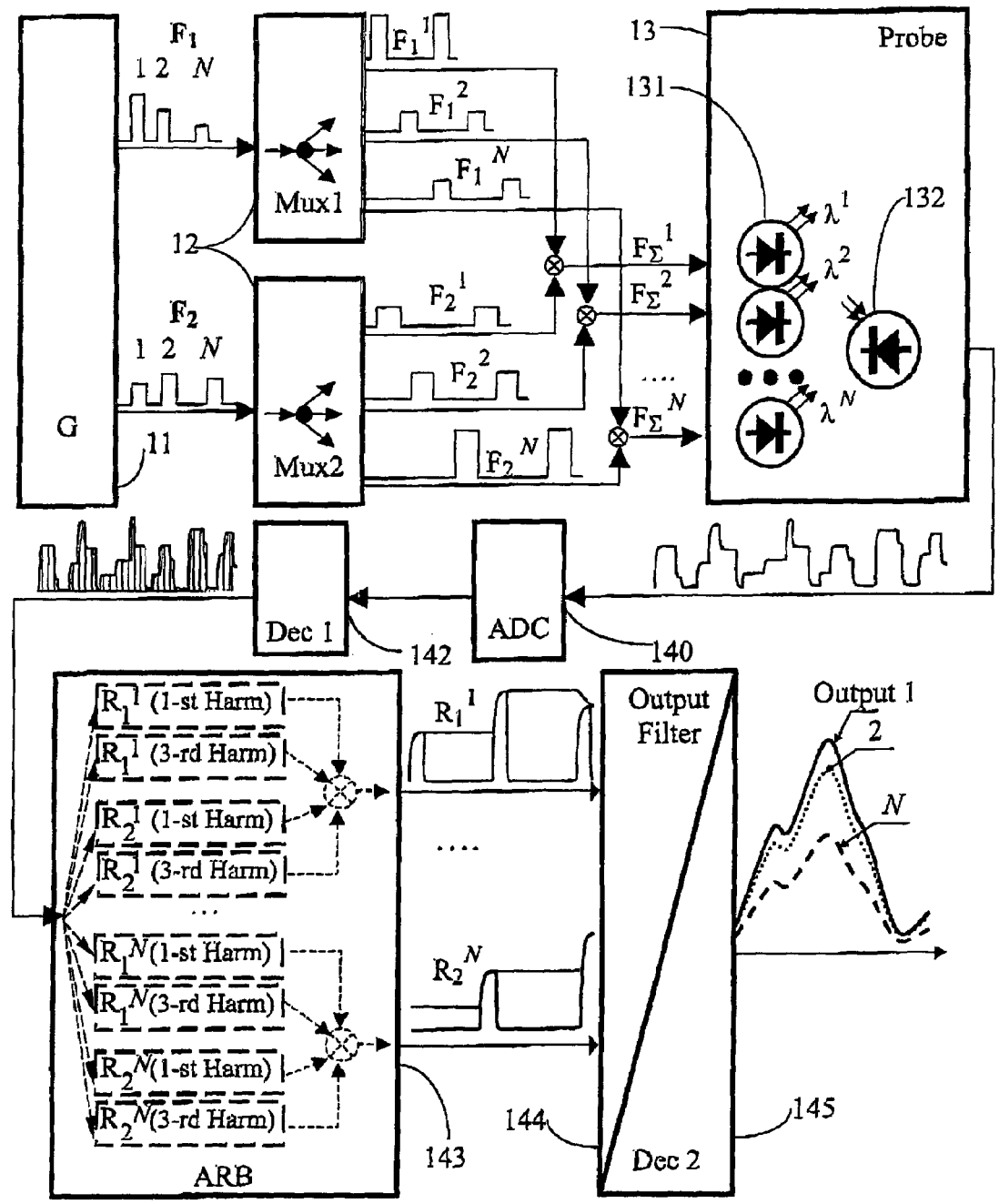
FIG. 8 is a schematic block diagram of a system of the present invention operating in a mixed-rate short serial mode regime, according to yet another example of the invention.
Figure 9:
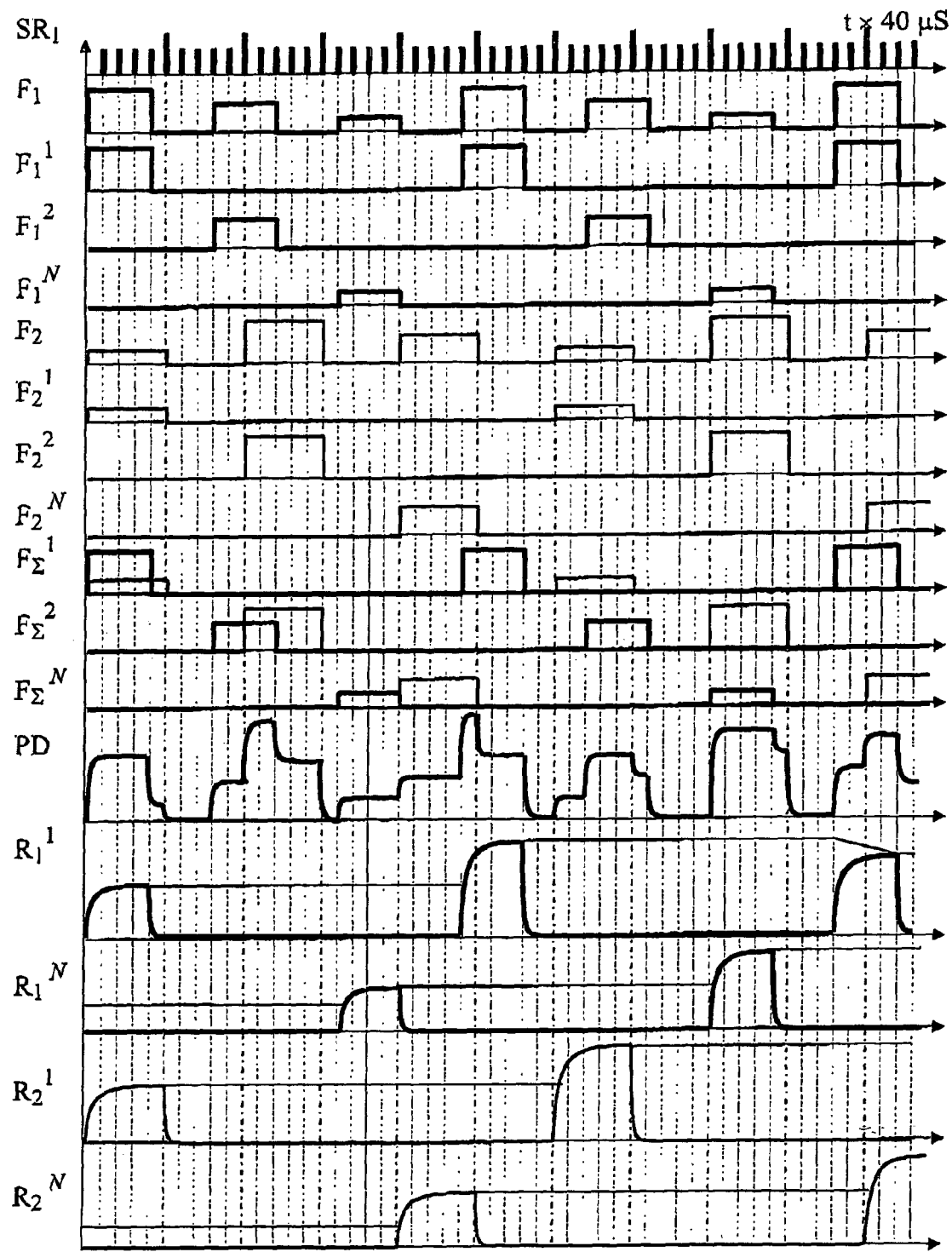
FIG. 9 illustrates an example of waveforms produced by different elements of the system shown in FIG. 8.

Referring to FIG. 8 and FIG. 9 together, another example of the system operating in a mixed-rate short serial rode regime and the corresponding waveforms are illustrated. According to this example, the modulation mode regime is different from those used in Examples 1 and 2.

The Generator 11 provides two pulse sequences $F_1$ and $F_2$ at rates of 3.125 kHz and 2.5 kHz, respectively. The MUX1 and MUX2 subdivide each of these two sequences into ten subsequences. In particular, the sequence $F_1$ corresponds to the signals $F_1^1, F_1^2, \ldots, F_1^N$, while the sequence $F_2$ corresponds to the signals $F_2^1, F_2^2, \ldots, F_2^N$.

The first short serial mode regime (the pulses $F_1^1, F_1^2, \ldots, F_1^N$) is applied to the N LEDs (where N=10) at the modulation frequency of 3.125 kHz, as in Example 1. The LED switch functions associated with the first sequence are denoted as $\chi_1^1, \ldots, \chi_1^N$. At the same time, another short serial mode regime (the pulses $F_2^1, F_2^2, \ldots, F_2^N$) is applied to the same N LEDs having the modulation rate of 2.5 kHz. Accordingly, the LED switch functions associated with the second sequence is denoted as $\chi_2^1, \ldots, \chi X_2^N$. In other words, the superposition of the pulses $F_1^1$ and $F_2^1$ drives the LED $\lambda_1$, the superposition of $F_1^2$ and $F_2^2$ drives the LED $\lambda_2$, etc. Finally, the superposition of the pulses $F_1^{10}$ and $F_2^{10}$ drives the LED $\lambda_{10}$.

According to this scenario, each LED is activated by a combination of two modulation sequences. This case is different from that of Example 1, because each LED receives a combined complex-form pulse sequence, rather than a simple square-pulse sequence.

At the receiver side, for the decomposition of the PD signal, the number of resonators properly increases. In particular, each recovered signal $R_r^l$ (r=1,2; l=1, . . . , N) needs two resonators, for the 1-st and the 3-rd harmonics, respectively. Each LED is triggered by the two subsequences, and therefore each channel needs four resonators (pairs of states), such as a resonator for the 1-st harmonic corresponding to the modulation frequency of 3.125 kHz, a resonator for the 3-rd harmonic of 3.125 kHz, a resonator for the 1-st harmonic of 2.5 kHz, and a resonator for the 3-rd harmonic of 2.5 kHz. Aggregation of these four resonators provides a total output signal for the corresponding channel.

Each resonator operates in the manner described above, under the control of the LED's switch function. The output signal is aggregated from the in-phase and quadrature of each resonator (as in Example 1), then it aggregates the 1-st and 3-rd harmonics (as in Example 2), and, finally, it combines outputs associated with the modulation pulses at different rates of 3.125 kHz and 2.5 kHz, correspondingly.

It should be appreciated by a person versed in the art that driving each LED by superposition of two modulation sequences can increase the measurement quality. This improvement can be achieved exclusively at the expense of moderate increase of computations, whereas the hardware remains the same. It is noteworthy that the mixed-rate scenario of Example 3 allows a reliable and accurate extraction of the signal components without significant interaction between the two concurrent frequencies of 2.5 kHz and 3.125 kHz.

It should be appreciated that despite the differences of the above examples, all of them can be implemented within the same DSP framework. A generalized algorithm implementing the method of the present invention complying with these three examples and other scenarios for decomposition of multi-channel signals is presented as follows.

Design Parameters:
Slow Convergence Parameter, $\epsilon_a$, $\epsilon_l$
Fast Convergence Parameter, $\gamma_a$, $\gamma_l$
Frequency Convergence Parameter, $\rho_a$, $\rho_l$
Forgetting Factor $\mu$
Fixed-Frequency Disturbances $\omega_d$, d=1, 2, . . . ;
Unknown Disturbances Initial Guess $\omega_u v$, u=1, 2, . . . ;
Modulation Rates $\omega_r$, r=1, 2, . . . ;
Indices of LEDs l=1, 2, . . . , N;
Indices of Harmonics k=1, 3, . . . ;
LED Switch Functions $X_r^l$, r=1, 2, . . . ; l=1, 2, . . . , N;
State Vector Designation:
$x_1$—dc (single state)
$x_2$—Nyquist (single state)
$x_3$—$1^{st}$ Modulation Rate, $1^{st}$ LED, $1^{st}$ Harmonic (in-phase & quadrature states) . . .
$x_i$—$r^{th}$ Modulation Rate, $l^{th}$ LED, $k^{th}$ Harmonic (in-phase & quadrature states) . . .
$x_p$—$d^{th}$ known-frequency disturbance $\omega_d$ (in-phase & quadrature states) . . .
$x_q$—$u^{th}$ unknown-frequency disturbance $\omega_u$ (in-phase & quadrature states) . . .
Transition Matrix of $i^{th}$ Resonator for $l^{th}$ LED, $r^{th}$ Modulation Rate & $k^{th}$ Harmonic
$C_i=\cos(k\omega_r)$, $S_i=\sin(k\omega_r)$, $$Ti = \begin{vmatrix} C_i & S_i \\ -S_i & C_i \end{vmatrix}$$

$C_i$ $S_i$ i=$i_{r,k,l}$, r=1, 2 . . . ; k=1, 3, . . . ; l=1, . . . , N
Transition Matrix of $p^{th}$ Resonator related to $d^{th}$ fixed-frequency Disturbance
$C_p=\cos(\omega_d)$, $S_p=\sin(\omega_d)$, $$T_p = \begin{bmatrix} C_p & S_p \\ -S_p & C_p \end{bmatrix}$$

p=$p_d$, d=1, 2, . . .

Fixed Part of Integrated Transition Matrix
$T_0=1\oplus(-1)\oplus bd(T_i, i=i_{r,k,l}, r=1, 2 . . . ; k=1, 3, . . . ; l=1, . . . , N)\oplus bd(T_p, p=p_d, d=1, 2, . . . )$
Fixed Part of Gain
$G_0=[\epsilon(1-1), \gamma(C_i, -S_i, . . . ), \epsilon(C_p, -S_p, . . . )]$
i=$i_{r,k,l}$, r=1, 2 . . . ; k=1, 3, . . . ; l=1, . . . , N
p=$p_d$, d=1, 2, . . . ;

Initialization for n=0:
Fast Relaxation Factor $\gamma(0)=\gamma_a$
Slow Relaxation Factor $\epsilon(0)=\epsilon_a$
Frequency Convergence Factor $\rho(0)=\rho_a$
Unknown Disturbance Frequency: $\omega_u(0)=\omega_{uv}$, u=1, 2, . . . ;

Compute For Time Instant n=1, 2, . . .
Current Observation Function
h=h(n)=[1, -1, $\chi_1^1$, 0, . . . , $\chi_r^l$, . . . , 1, 0, . . . , 1, 0]
Current State Update Function
$\chi=\chi(n)=[1, 1, \chi_1^1, 0 . . . , \chi_r^l, 0, . . . , 1, 0, . . . , 1, 0]$
Transition Matrix of Resonator related to $u^{th}$ Varying-frequency Disturbance
$C_q=\cos(\omega_u)$, $S_q=\sin(\omega_u)$, $$T_q = \begin{bmatrix} C_q & S_q \\ -S_q & C_q \end{bmatrix}$$

q=$q_u$, u=1, 2, . . .
Integrated Transition Matrix (Updated)
$T=T_0\oplus bd(T_q, q=q_u, u=1, 2, . . .)$
Updated Gain
$G=[G_0, \epsilon(C_q, -S_q, . . . )]$, q=$q_u$, u=1, 2, . . . ;
x(n+1|n)=Tx(n)—Prediction
e(n)=y(n)−h(n)x(n+1|n)—Prediction Error
x(n+1)=x(n+1|n)+$\chi$(n)Ge(n)—State Update
Amplitude Related to $l^{th}$ LED, l=1, . . . , N
(Computed From In-Phase/Quadrature Components and Used Harmonics)
$A_l$=sqrt($\Sigma c_i^2+\Sigma s_i^2$), i=$i_{r,k,l}$, r=1, 2 . . . ; k=1, 3, . . . ;
Unknown Disturbance Phase
$\phi_q(n+1)=\arctan(c_q/s_q)+k_q\pi$, q=$q_u$, u=1, 2, . . . ;
$k_q$ is an unwrapping factor preventing higher than $\pi$ jumps in $\phi_q(n+1)$ compared to the preceding termi $\phi_q(n)$.
Unknown Frequency Update
$\omega_q(n+1)=\rho\omega_q(n)+(1-\rho)[\phi_q(n+1)-\phi_q(n)]$, q=$q_u$, u=1, 2, . . . ;
Relaxation Factors:
$\gamma=\rho\gamma+(1-\mu)\gamma_1$, $\epsilon=\mu\epsilon+(1-\mu)\epsilon_1$, $\rho=\mu\rho+(1-\mu)\rho_1$
End of the loop In the above algorithm, the symbol $\oplus$ denotes block diagonal matrix expansion operator, while the symbol bd(.) relates to the block diagonal matrix composed of its parameters.

As such, those skilled in the art to which the present invention pertains, can appreciate that while the present invention has been described in terms of several embodiments, the concept upon which this disclosure is based may readily be utilized as a basis for the designing of other structures, systems and processes for carrying out the several purposes of the present invention.

It will also be understood that the system according to the invention may be a suitably programmed computer. Likewise, the invention contemplates a computer program being readable by a computer for executing the method of the invention. The invention further contemplates a machine-readable memory tangibly embodying a program of instructions executable by the machine for executing the method of the invention.

Also, it is to be understood that the phraseology and terminology employed herein are for the purpose of description and should not be regarded as limiting.

In the method claims that follow, alphabetic characters and Roman numerals used to designate claim steps are provided for convenience only and do not imply any particular order of performing the steps.

Finally, it should be noted that the word "comprising" as used throughout the appended claims is to be interpreted to mean "including but not limited to".

It is important, therefore, that the scope of the invention is not construed as being limited by the illustrative embodiments set forth herein. Other variations are possible within the scope of the present invention as defined in the appended claims and their equivalents.

The invention claimed is:

1. A method for decomposition of a multiple channel signal reflecting characteristics of a blood perfused fleshy medium for use in determination of at least one desired blood parameter, the method comprising:
    (a) illuminating a portion of the medium by amplitude-modulated light of more than two different optic channels having wavelength in a range where the scattering properties of blood are sensitive to light radiation;
    (b) sensing a light response of the medium and generating said multiple channel signal; and
    (c) analyzing said multiple channel signal, where the analyzing includes:
        (i) filtering said multiple channel signal and separating at least a part of multiple channels from each other; and
        (ii) providing time evolutions of the light responses of the medium for the part of said multiple channels, the method, wherein
        said amplitude-modulated light is activated in a composite mode regime selected from the group consisting of a short serial-parallel mode regime and a mixed-rate short serial mode regime; and
        the filtering of said multiple channel signal and the separating of said multiple channels from each other both include applying an adaptive resonator bank to said multiple channel signal.

2. The method of claim 1 further comprising deriving at least one blood characteristic parameter as a relation between the different time evolutions of the light responses of the medium.

3. The method of claim 1 wherein the analyzing of said multiple channel signal includes digitizing thereof.

4. The method of claim 1 wherein the analyzing of said multiple channel signal includes sampling thereof.

5. The method of claim 1 wherein the analyzing of said multiple channel signal includes decimating thereof.

6. The method of claim 1 wherein the providing of said time evolutions of the light responses includes filtering sinusoid signals corresponding to the optic channels, thereby obtaining light intensity signals therefor.

7. The method of claim 1 wherein said adaptive resonator bank is a closedloop resonator bank with frequency adjustment.

8. The method of claim 7 wherein said closed-loop resonator bank is realized as a spectral observer configured for separation of optic channels from each other.

9. The method of claim 7 wherein said closed-loop resonator bank includes spectral observer states configured for filtering out signal trends.

10. The method of claim 7 wherein said closed-loop resonator bank includes spectral observer states configured for filtering out corresponding optical and electromagnetic disturbances of the signal.

11. The method of claim 7 wherein said closed-loop resonator bank is realized as a spectral observer configured for filtering out a noise signal.

12. A system for determination of at least one blood parameter of a blood perfused fleshy medium, the system comprising:
    (i) a generator for providing a train of activating pulses;
    (ii) a multiplexer (MUX) coupled to the generator configured for switching the activating pulses between different optic channels, wherein said switching is carried out in a composite mode regime for said activating pulses selected from the group consisting of a short serial-parallel mode regime and a mixed-rate short serial mode regime;
    (iii) a probe including:
        (a) an illumination assembly having a plurality of light sources coupled to the MUX and activated by said activating pulses for generating amplitude-modulated light of more than two different optic channels having wavelength in a range where the scattering properties of blood are sensitive to light radiation, and
        (b) a photodetector adapted for sensing a light response of the medium and generating a multiple channel signal reflecting blood characteristics;
    (iv) an analyzer configured for analyzing said multiple channel signal, wherein the analyzer includes a digital signal processor having:
        (a) an adaptive resonator bank unit configured for filtering said multiple channel signal and separating at least a part of multiple channels from each other; and
        (b) an output filtering unit configured for obtaining time evolutions of the light responses of the medium for the part of said multiple channels.

13. The system of claim 12 wherein said composite mode regime is a short serial-parallel mode regime.

14. The system of claim 12 wherein said composite mode regime is a mixed-rate short-serial mode regime.

15. The system of claim 12 wherein said analyzer includes an analog-to-digital converter for digitizing and high-rate sampling said multiple channel signal.

16. The system of claim 12 wherein said analyzer includes a first decimator for decimating the signal after the initial high-rate sampling.

17. The system of claim 12 wherein said analyzer includes a second decimator configured for outputting said time evolutions of the light responses at a lower sampling rate.

18. The system of claim 12 wherein a synchronization is provided between the illumination assembly and the adaptive resonator bank.

19. The system of claim 12 wherein said adaptive resonator bank is a closed-loop resonator bank with frequency adjustment.

20. The system of claim 19 wherein said closed-loop resonator bank is realized as a spectral observer configured for separation of optic channel from each other.

21. The system of claim 19 wherein said closed-loop resonator bank is realized as a spectral observer configured for filtering out signal trends.

22. The system of claim 19 wherein said closed-loop resonator bank is realized as a spectral observer configured for filtering out corresponding optical and electromagnetic disturbances of the signal.

23. The system of claim 19 wherein said closed-loop resonator bank is realized as a spectral observer configured for filtering out a noise signal.

24. A program storage device readable by machine, tangibly embodying a program of instructions executable by the machine to perform method steps for decomposition of a multiple channel signal reflecting characteristics of a blood perfused fleshy medium for use in determination of at least one desired blood parameter, where said multiple channel signal being generated in response to illuminating a portion of the medium by amplitude-modulated light of more than two different optic channels having wavelength in a range where the scattering properties of blood are sensitive to light radiation, the method steps comprising:

analyzing said multiple channel signal, where the analyzing includes:
(i) filtering said multiple channel signal and separating at least a part of multiple channels from each other; and
(ii) providing time evolutions of the light responses of the medium for the part of said multiple channels, the method steps, wherein
said amplitude-modulated light is activated in a composite mode regime selected from the group consisting of a short-serial-parallel mode regime and a mixed-rate short serial mode regime; and
the filtering of said multiple channel signal and the separating of said multiple channels from each other both include applying an adaptive resonator bank to said multiple channel signal.

25. A computer program product comprising a computer useable medium having computer readable program code embodied therein for decomposition of a multiple channel signal reflecting characteristics of a blood perfused fleshy medium for use in determination of at least one desired blood parameter, where said multiple channel signal being generated in response to illuminating a portion of the medium by amplitude-modulated light of more than two different optic channels having wavelength in a range where the scattering properties of blood are sensitive to light radiation, the computer program product comprising:

computer readable program code for causing the computer to analyze said multiple channel signal, where the analyzing includes:
filtering said multiple channel signal and separating at least a part of multiple channels from each other; and
providing time evolutions of the light responses of the medium for the part of said multiple channels, wherein
said amplitude-modulated light is activated in a composite mode regime selected from the group consisting of a short serial-parallel mode regime and a mixed-rate short serial mode regime; and
the filtering of said multiple channel signal and the separating of said multiple channels from each other both include applying an adaptive resonator bank to said multiple channel signal.

* * * * *